(12) United States Patent
Reinmüller et al.

(10) Patent No.: US 7,902,171 B2
(45) Date of Patent: Mar. 8, 2011

(54) COMPOSITION FOR TREATING INFLAMMATORY DISEASES

(76) Inventors: Johannes Reinmüller, Wiesbaden (DE); Kay Dirting, Wiesbaden (DE)

( * ) Notice: Subject to any disclaimer, the term of this patent is extended or adjusted under 35 U.S.C. 154(b) by 175 days.

(21) Appl. No.: 10/586,345

(22) PCT Filed: Jan. 12, 2005

(86) PCT No.: PCT/EP2005/000215
§ 371 (c)(1), (2), (4) Date: Jul. 14, 2006

(87) PCT Pub. No.: WO2005/067944
PCT Pub. Date: Jul. 28, 2005

(65) Prior Publication Data
US 2008/0188441 A1 Aug. 7, 2008

(30) Foreign Application Priority Data
Jan. 14, 2004 (DE) .......................... 10 2004 002 001

(51) Int. Cl.
*A01N 43/04* (2006.01)
*A61K 31/715* (2006.01)
(52) U.S. Cl. ......................................................... 514/54
(58) Field of Classification Search .................... 514/54
See application file for complete search history.

(56) References Cited

U.S. PATENT DOCUMENTS

| | | | |
|---|---|---|---|
| 4,141,973 A | | 2/1979 | Balazs et al. |
| 4,713,448 A * | 12/1987 | Balazs et al. ................ 536/55.1 |
| 4,716,224 A * | 12/1987 | Sakurai et al. ............... 536/55.1 |
| 5,679,655 A * | 10/1997 | Gallina .......................... 514/54 |
| 5,728,391 A | 3/1998 | Ikeya et al. |
| 5,830,882 A | 11/1998 | Falk et al. |
| 5,910,489 A | 6/1999 | Falk et al. |
| 5,914,322 A * | 6/1999 | Falk et al. ...................... 514/54 |
| 6,455,066 B1 * | 9/2002 | Fischer et al. ................ 424/449 |
| 2004/0136925 A1 * | 7/2004 | Petrigni et al. ................. 424/49 |
| 2005/0043271 A1 | 2/2005 | Gross et al. |
| 2005/0137164 A1 * | 6/2005 | Arkin et al. ...................... 514/54 |
| 2005/0164979 A1 | 7/2005 | Gross et al. |
| 2005/0187185 A1 | 8/2005 | Reinmuller |

FOREIGN PATENT DOCUMENTS

| | | |
|---|---|---|
| DE | 102 09 966 A1 | 5/2003 |
| DE | 10209966 A1 * | 5/2003 |
| EP | 0161887 B1 | 9/1991 |
| EP | 0 715 852 A | 6/1996 |
| WO | WO 00/44367 A | 8/2000 |
| WO | WO-03 049747 A1 | 6/2003 |
| WO | WO-03 053452 A1 | 7/2003 |

OTHER PUBLICATIONS

Definition of prevention, Merriam-Webster Online Dictionary [retrieved: Aug. 15, 2008].*
Definition of "inflammation" from Stedman's Medical Dictionary. [online, retrieved on Oct. 7, 2008].*
Leshchinskii, a.f., Zuza, Z.I., Barkagan, T.S. (1972) Pathogenesis of inflammation and mechanism of the anti-inflammatory action of experimental pelotherapy. Bulletin of Experimental Biology and Medicine, vol. 73, No. 4, p. 384-387.*
Wilkinson, G.R. (2001) "Pharmacokinetics, The Dynamics of Drug Absorption, Distribution, and Elimination" in Goodman and Gilman's The Pharmacological Basis of Therapeutics. editors Joel G. Hardman and lee E. Limbird, published by The McGraw-Hill Companies, Inc., p. 24-26.*
Sterling, J.C., Handfield-Jones, S., Hudson, P.M. (2001) Guidelines for the management of cutaneous warts. British Journal of Dermatology, vol. 144, p. 4-11.*
Stanberry, L.R. (1991) Evaluation of Herpes Simplex Virus Vaccines in Animals: The Guniea Pig Vaginal Model. Reviews of Infectious Diseases, vol. 13, No. 11, p. S920-S923.*
"Artificial Skin Powder Composition Containing Sodium Hyaluronate and Its Preparation"; Derwent, Jul. 25, 2000, XP002232150.
Volpi, Nicola et al., "Role, Metabolism, Chemical Modifications and Applications of Hyaluronan," Current Medicinal Chemistry, 2009, vol. 16, pp. 1718-1745.

* cited by examiner

*Primary Examiner* — Shaojia Anna Jiang
*Assistant Examiner* — Scarlett Goon
(74) *Attorney, Agent, or Firm* — Millen, White, Zelano & Branigan, P.C.

(57) ABSTRACT

The present invention relates to the use of hyaluronic acid for treating inflammatory diseases, in particular skin or mucous membrane diseases.

14 Claims, No Drawings

COMPOSITION FOR TREATING INFLAMMATORY DISEASES

The present invention relates to the use of hyaluronic acid for treating inflammatory diseases, in particular skin diseases or mucous membrane diseases.

A great number of skin diseases, in particular those of the atopic type, have not been explained causally. Commonly, these diseases are inflammatory reactions of the dermis and of the dermoepithelial transition zone. It is known that in these diseases considerable shifts in the normal hyaluronic acid content in the dermis and epidermis occur. The treatment of such diseases at present consists in various measures, e.g. administration of fat-containing ointments, creams or lotions with addition of different active compounds. Most effectively, such inflammatory diseases, however, are treated with corticoid-containing preparations for external (topical) use. The adequately known local and systemic side effects of the corticoids (derivatives of the endogenous steroid hormone cortisol) are to be expected here. In the case of chronic use of the topical corticoid preparations, as a rule delayed consequences occur, such as, for example, cutaneous atrophy.

Another means of treatment consists in the use of agents which attack cells of the immune system and inhibit the biosynthesis of immunomodulators, such as, for example, cyclosporin, tacrolism and pimecrolism. Substances having such actions are also described as immunosuppressants, because they suppress the immune response of a bioorganism. Their use is thus considerably restricted, since an intact immune system is essential for a permanently satisfactory state of health. Use is thus suitable only in the case of severe symptoms and in physically mature individuals. Long-term risks and the risks of long-term use, such as, for example, carcinogenicity, are completely unexplained.

There is therefore a need to develop new agents for treating inflammatory skin diseases or mucous membrane diseases, in which the disadvantages of the prior art can be at least partly avoided.

Surprisingly, it has been found that hyaluronic acid, a glycosaminoglycan, is outstandingly suitable for treating inflammatory skin diseases or mucous membrane diseases, in particular of inflammatory skin diseases of the atopic type.

One subject of the invention is thus the use of hyaluronic acid for the production of a composition for preventing or treating inflammatory skin diseases or mucous membrane diseases.

A further subject of the invention is a process for preventing or treating an inflammatory skin or mucous membrane disease, where a preparation is administered to a subject to be treated, for example a human patient or alternatively an animal, which contains hyaluronic acid in an amount adequate for treating the disease.

The administration of hyaluronic acid can in principle be carried out in any desired manner, provided this is suitable for treating the respective disease. In many cases, local administration is carried out in the area of the diseased skin site, e.g. a lesion. Preferably, administration is carried out intradermally, e.g. by injection, or by topical application to the diseased skin site.

For the treatment of inflammatory skin diseases, hyaluronic acid is suitable both in uncrosslinked form and in crosslinked form or mixtures thereof. Uncrosslinked hyaluronic acid is preferably selected from (i) long-chain hyaluronic acid having an average molecular weight (weight-average) of at least 200 kD and (ii) short-chain hyaluronic acid having an average molecular weight (weight-average) up to 50 kD or mixtures thereof.

Crosslinked hyaluronic acid can be, for example, covalently or noncovalently crosslinked. The preparation of crosslinked hyaluronic acid can be carried out per se in a known manner. Covalent crosslinkage can in general be carried out here by crosslinking with bifunctional reactive agents, such as, for example, glutaraldehyde or carbodiimide, via bifunctional amino acids, e.g. lysine, protamines or albumins. It is also possible, however, to produce crosslinkages by means of an amide, ester or ether bond for example. Further suitable reagents for the covalent crosslinkage of hyaluronic acid are ethylene glycol diglycidyl ether or 1,4-butanediol diglycidyl ether, divinyl sulfone, photocrosslinking reagents, such as ethyleosin, hydrazides, such as bishydrazide, trishydrazide and polyvalent hydrazide compounds. Furthermore, intra- or/and intermolecularly esterified hyaluronic acid derivatives can also be employed. A noncovalent crosslinkage using multivalent metal ions, such as, for example, iron, copper, zinc, calcium, magnesium, barium and other chelating metal ions is particularly preferred.

Hyaluronic acid is commercially obtainable in the crosslinked state (e.g. Hylaform®, a crosslinked hyaluronic acid from Biomatrix, N.J., USA; for preparation see also U.S. Pat. No. 4,713,448, U.S. Pat. No. 4,605,691, APC® from Fidia, Incert® from Anika Therapeutics, Intergel® from LifeCore or Restylane from Q-Med).

In use, the molecular weight and, in the case of crosslinked hyaluronic acid products, the degree of crosslinkage is of importance which, for example, is in the range from 0.1% to 10%, without being restricted thereto. Generally, it is to be observed that with long-chain hyaluronic acid a lower degree of crosslinking suffices in order to obtain a gelatinous matrix, whereas with short-chain hyaluronic acid a higher degree of crosslinkage is necessary in order to obtain comparable properties.

The hyaluronic acid preparation according to the invention can be employed both in human medicine and in veterinary medicine, for example for treating domestic animals or agricultural animals.

The pharmaceutical compositions according to the invention contain the hyaluronic acid preferably in amounts from 0.01 to 20% by weight, based on the total pharmaceutical composition, in particular in an amount from 0.01 to 5% by weight and particularly preferably in an amount from 0.01 to 1% by weight.

As pharmaceutical excipients, the pharmaceutical compositions according to the invention can contain, for example, agents for pH adjustment, stabilizing agents, antioxidants, solubilizers, penetration-promoting agents, preservatives or/and gel-forming agents, such as are customarily used in such compositions. They are used in the amounts customary in such preparations.

In addition to the active compound hyaluronic acid, the pharmaceutical compositions according to the invention can optionally also contain still further pharmaceutical active compounds which are compatible with hyaluronic acid in the course of application, e.g. active compounds for the therapy of skin diseases (dermatoses), antimycotics, antibiotics (e.g. gentamycin, vancomycin, penicillins or cephalosporins), sulfonamides; disinfectants, hormones (e.g. corticoids) and hormone derivatives (e.g. cortisol), local anesthetics (of the lidocaine or novocaine type), vasoactive substances for vasoconstriction (avoidance of hemorrhages), adrenalin, enzymes (such as, for example, hyaluronidase), interleukins, growth factors (e.g. EGF, PDGF or/and IGF), vitamins (e.g. vitamin D), skincare agents and/or circulation-promoting (hyperemizing) agents. The further active compounds can optionally be associated with the hyaluronic acid, e.g. by covalent or non-covalent interactions.

Also of importance are additives, such as, for example, di- or trivalent metal ions, which can have a crosslinking and stabilizing action as a result of chelate formation, which on the other hand can also accelerate the degradation of the active hyaluronic acid.

In the tissue, the degradation of hyaluronic acid is carried out naturally by a large number of different hyaluronidases or by oxygen free radicals. Therefore additives which have an inhibitory action on hyaluronidases (heparin, indomethacin or/and salicylates) and those which prevent the oxidative degradation of hyaluronic acid in the tissue as "free radical traps" (vitamins A, E or/and C) are furthermore of importance.

A particularly preferred embodiment of the preparation according to the invention are mixtures of long-chain hyaluronic acid (>200 kD) with short-chain hyaluronic acid (e.g. hexamers of the repetitive disaccharide units or larger units up to 50 kD) or alternatively mixtures of the aforementioned with crosslinked hyaluronic acid. Viscous injectable preparations result here, which are preferably introduced intradermally using injection needles (e.g. 30 gauge) or extensively by injection on the border of the dermoepidermal transition. The raising of isolated weals is also suitable according to the invention. The known local anesthetics can be added to the injectable hyaluronic acid preparations for minimization of the painfulness of the injection.

A further particularly preferred embodiment are mixtures of crosslinked hyaluronic acid and noncrosslinked hyaluronic acid.

Instead of the injection technique using needles, the preparations according to the invention can also be administered extremely effectively by pressure injection. This process is distinguished by extensive freedom from pain.

Further preparations according to the invention of the active compound are aqueous solutions or emulsions for intravenous administration or for instillation into body cavities or hollow organs.

Since the barrier function of the dermoepithelial transition and of the deeper epidermal layers is disturbed by the inflammatory process of the entire skin in the case of one of the aforementioned diseases, the preparations according to the invention can also be applied topically, i.e. superficially, to the skin in the form of ointments, creams, lotions, gels, sprays, tinctures, shampoos or occlusive films. A particular form of preparation within the meaning of the invention is a dry hyaluronic acid preparation in the form of a powder, which is used in particular for treating weeping eczema. The invention also relates to the introduction of the active compounds in micro-encapsulated form or in the form of liposomes. A large number of such topical preparations are known from the cosmetics field, these substances being applied exclusively to healthy and intact skin.

Surprisingly, it has emerged that on use according to the invention of such topical preparations on inflammatory skin, an exacerbation, for example, does not occur, but a regression of the inflammatory symptoms. If mucous membranes of the airways have to be treated, aerosols can also be employed according to the invention as inhalation solutions.

The compositions according to the invention can be prepared in a generally known manner, which is customary per se for the preparation of such compositions. Here, the sequence of the mixing of the individual constituents is not critical as a rule.

The nature, dose and the frequency of the administration of the composition according to the invention and the condition (e.g. viscosity, degree of crosslinking, active compound content etc.) depend in particular on the nature and severity of the disease and on the age of the patient and the place and the nature of the application, e.g. the condition and the sensitivity of the inflamed site. If the compositions according to the invention are administered in the form of topically applicable preparations, the administration as a rule conforms to the conditions customary for such compositions.

The nature of the treatment and the frequency of application in particular also depend on the individual responses of the persons to be treated. Preferably, an application of gels or solutions takes place at intervals of several days up to one or two months, in particular about one to two weeks.

The invention also comprises mixtures of hyaluronic acid with other glycosaminoglycans in crosslinked or/and non-crosslinked form. For possible combinations and crosslinking possibilities, reference is made to EP-B-0 619 737, DE-A-102 99 66 and WO 03/041723. Mixtures of hyaluronic acid and heparin are preferred. Mixtures of hyaluronic acid and positively charged glycosaminoglycans, such as chitosamine, are furthermore preferred.

The following skin diseases can be treated particularly successfully using the preparations according to the invention: atopic dermatitis and eczematous skin diseases, such as seborrheic eczema and microbial eczema, pruritus, prurigo, urticaria, red lichen, psoriasis, such as psoriasis vulgaris, vitiligo, rosacea, perioral dermatitis, acne vulgaris or acne conglobata, and chronic and acute ulcerations of the skin. In addition, the composition is suitable for supportive treatment in mycoses, in particular in combination with an antimycotic.

Surprisingly, viral skin diseases which lead to wart formation can also be favorably influenced using the preparations according to the invention, such as, for example, verruca vulgaris, condylomas, such as, for example, vulvar warts (Condylomata accuminata), or other pathological skin symptoms caused by viruses of the papilloma group. Hyaluronic acid is preferably injected here at the base of such lesions on the dermoepidermal transition. The action of hyaluronic acid on herpes viruses was known (see patent application WO 03/041723).

A further group of diseases of the mucous membranes are "aphthae". Painful vesicles are formed on the mucous membranes here. The cause of aphthae formation is hitherto unknown. The use according to the invention of hyaluronic acid in the case of aphthae lead to an immediate regression of the painfulness and to subsequent healing of the aphthae.

The uses of hyaluronic acid for the prevention or treatment of diseases of mucous membranes or of body openings which are lined with these is also expressly regarded as a subject of the invention. In this connection, suitable gelatinous preparations can be instilled into appropriate cavities or the mucous membrane lesions can be lined submucosally by suitable techniques. Treatment successes can be achieved, for example, in polypous mucous membrane diseases, such as nasal polyposis, or in inflammatory intestinal diseases. The submucosal administration of the active compound can in this case also be carried out endoscopically.

The use of the preparation according to the invention extends not only to the introduction into dermis and epidermis. In particular cases, the application of the preparation according to the invention under the dermis can also be necessary and is thus a use within the meaning of the invention. The introduction of the active compound into closed body cavities, such as, for example, chest and abdominal cavity, is also according to the invention.

A further subject of the invention is the use of a preparation which contains a mixture of crosslinked and noncrosslinked hyaluronic acid for cosmetic or pharmaceutical uses, in particular for treating skin or soft tissue defects, and also wrinkles of the skin.

From the use of crosslinked hyaluronic acid for the lining of skin wrinkles and similar defects, the side effects known are inflammatory reactions which appear in the form of redness, swelling, burning, itching and with the formation of small intradermal nodules. These side effects can be suppressed according to the invention by admixing noncrosslinked hyaluronic acid to the preparations of exclusively crosslinked hyaluronic acid. Admixtures of low molecular weight fractions up to about 500 kD have proven favorable here. The protective effect, however, can also be achieved using noncrosslinked hyaluronic acid above the molecular size mentioned, it also being possible to employ fractions up to 5 million D. Therefore, mixtures of crosslinked and noncrosslinked hyaluronic acid for employment in the cosmetic or pharmaceutical treatment of wrinkles, soft tissue defects and for the augmentative treatment of soft tissues (e.g. lips) are likewise a subject of the invention. With regard to further preferred embodiments for this subject, reference is made to the details above.

The use according to the invention also includes the employment of hyaluronic acid on the conjunctiva of the eye and of the cornea, hitherto only the use of noncrosslinked hyaluronic acid after laser ablation of the cornea being known. It has been shown that crosslinked hyaluronic acid and mixtures of crosslinked and noncrosslinked hyaluronic acid can also be employed in manipulations, injuries and inflammations of the cornea. In the case of shaping treatments on the cornea of the eye, the employment of hyaluronic acid between the cornea and shaping dish for the purpose of an improvement of the visual power is also described as according to the invention. In the implantation of plastic lenses into the eye for the elimination of cataract, at present noncrosslinked hyaluronic acid is applied to the surface of the plastic lens for lubrication. The application of the preparation according to the invention, in particular of a mixture of noncrosslinked and crosslinked hyaluronic acid, optionally in combination with a further glycosaminoglycan, such as heparin, is more advantageous as a result, in that the postoperative inflammatory reaction is suppressed long-term and thus the occurrence of "after-cataract" is prevented. On the conjunctiva of the eye, according to the invention all inflammatory changes, that is inflammation of the conjunctiva or conjunctivitis, are favorably influenced. With regard to further preferred embodiments for this subject, reference is made to the details above.

USE EXAMPLES

Example 1

A 30 year-old female patient having atopic dermatitis was treated according to the invention by extensively introducing by injection 0.1 ml of a long-chain hyaluronic acid (Hyal System, Merz, Frankfurt/M) intradermally under atopic lesions in the area of the elbow. As early as 3 days after treatment, the previously excruciating itching had subsided. The original inflammatory symptoms were clearly declining.

Example 2

In a 14 year-old, a virus wart on the right index finger was intralesionally infiltrated with 0.1 ml of crosslinked hyaluronic acid (Juvederm 18, LEA Derm, Hallbergmoos). After 4 weeks, intact skin without wart attack existed in the treated region.

Example 3

The attacked skin areas of a 20 year-old man with acne vulgaris on the face were intradermally injected 0.75 ml deep with Hylaform. After 4 weeks, the acute inflammatory changes of the skin had disappeared. A fresh occurrence of the disease was able to be suppressed for 6 months.

The invention claimed is:

1. A method for treating an inflammatory skin or mucous membrane disease, comprising administering intradermally to a subject in need thereof an effective amount of hyaluronic acid in crosslinked form, which is not administered in conjunction with a penetration-promoting agent,
    wherein the inflammatory skin or mucous membrane disease is a viral skin disease which leads to wart formation, verruca vulgaris, or Condylomata accuminata.

2. A method according to claim 1, wherein administering is by local administration.

3. A method according to claim 1, wherein administering is to the border of the dermoepithelial transition.

4. A method according to claim 1, wherein the degree of crosslinking is 0.1% to 10%.

5. A method according to claim 1, wherein the subject is a human.

6. A method according to claim 1, wherein the subject is a veterinary patient.

7. A method according to claim 1, wherein the inflammatory skin or mucous membrane disease is a viral skin disease which leads to wart formation.

8. A method according to claim 1, wherein the hyaluronic acid is present as an injectable preparation.

9. A method according to claim 1, wherein the hyaluronic acid is in a composition which contains a further glycosaminoglycan in crosslinked or uncrosslinked form.

10. A method according to claim 1, wherein the hyaluronic acid is in a composition which contains an inhibitor of hyaluronic acid degradation.

11. A method according to claim 10, wherein the inhibitor of hyaluronic acid degradation is heparin, indomethacin, a salicylate, a free radical trap, or vitamin A, C or E, or a mixture thereof.

12. A method for treating an inflammatory skin or mucous membrane disease, comprising administering intradermally to a subject in need thereof an effective amount of a mixture comprising crosslinked and uncrosslinked hyaluronic acid,
    wherein the inflammatory skin or mucous membrane disease is a viral skin disease which leads to wart formation, verruca vulgaris, or Condylomata accuminata.

13. A method according to claim 12, wherein the uncrosslinked hyaluronic acid is
    (i) long-chain hyaluronic acid having an average molecular weight (weight-average) of at least 200 kD, or (ii) short-chain hyaluronic acid having an average molecular weight (weight-average) up to 50 kD, or (iii) a mixture thereof.

14. A method for treating an inflammatory skin or mucous membrane disease, comprising administering intradermally to a subject in need thereof an effective amount of a mixture comprising crosslinked and uncrosslinked hyaluronic acid, wherein the uncrosslinked hyaluronic acid is (a) short-chain hyaluronic acid having an average molecular weight (weight-average) up to 50 kD, or (b) a mixture of long-chain hyaluronic acid having an average molecular weight (weight-average) of at least 200 kD, and short-chain hyaluronic acid having an average molecular weight (weight-average) up to 50 kD, wherein the inflammatory skin or mucous membrane disease is a viral skin disease which leads to wart formation, verruca vulgaris, or Condylomata accuminata.

* * * * *